(12) United States Patent
Levine et al.

(10) Patent No.: US 7,815,591 B2
(45) Date of Patent: Oct. 19, 2010

(54) ATRAUMATIC GASTROINTESTINAL ANCHOR

(75) Inventors: Andy H. Levine, Newton, MA (US);
John C. Meade, Mendon, MA (US);
David A. Melanson, Hudson, NH (US)

(73) Assignee: GI Dynamics, Inc., Lexington, MA (US)

( * ) Notice: Subject to any disclaimer, the term of this patent is extended or adjusted under 35 U.S.C. 154(b) by 103 days.

(21) Appl. No.: 11/229,352

(22) Filed: Sep. 16, 2005

(65) Prior Publication Data

US 2006/0064120 A1    Mar. 23, 2006

Related U.S. Application Data

(60) Provisional application No. 60/611,038, filed on Sep. 17, 2004.

(51) Int. Cl.
*A61M 5/00* (2006.01)
*A61F 2/04* (2006.01)

(52) U.S. Cl. .................. 604/8; 623/23.64; 623/23.65
(58) Field of Classification Search ............. 606/153; 623/23.64, 23.7, 23, 64, 1.13; 604/8, 9
See application file for complete search history.

(56) References Cited

U.S. PATENT DOCUMENTS

| | | | |
|---|---|---|---|
| 1,899,781 A | 2/1933 | Twiss | |
| 2,464,933 A | 3/1949 | Kaslow | |
| 3,780,740 A | 12/1973 | Rhea | |
| 4,133,315 A | 1/1979 | Berman et al. | |
| 4,134,405 A | 1/1979 | Smit | |
| 4,246,893 A | 1/1981 | Berson | |
| 4,265,694 A | 5/1981 | Boretos et al. | |
| 4,270,542 A | 6/1981 | Plumley | |
| 4,271,827 A | 6/1981 | Angelchik | |
| 4,279,251 A | 7/1981 | Rüsch | |

(Continued)

FOREIGN PATENT DOCUMENTS

DE    33 26 061 A1    2/1984

(Continued)

OTHER PUBLICATIONS

WO 00/42945 Al-Saadon, Khalid, Published Jul. 27, 2000; "Expandable Endovascular Medical Tubular Stent".*

(Continued)

*Primary Examiner*—Todd E Manahan
*Assistant Examiner*—Michael G Mendoza
(74) *Attorney, Agent, or Firm*—Hamilton, Brook, Smith & Reynolds, P.C.

(57) ABSTRACT

The present invention relates to methods and articles for anchoring within a natural bodily lumen. An anchor is adapted to provide differing radially-outward forces along its length, a securing force and a transitional force. Production of these forces can be controlled by varying a physical property of the anchor, such as its stiffness, thickness, or shape. For example, the stiffness of an elongated anchor can be varied from a relatively soft value at its proximal and distal ends to a relatively stiff value at its center by varying the diameter of wire forming the anchor, thereby tailoring it to an intended application. Such force tailoring can be combined with external barbs and used to reliably anchor other instruments, such as feeding tubes and intestinal sleeves.

29 Claims, 10 Drawing Sheets

U.S. PATENT DOCUMENTS

| | | |
|---|---|---|
| 4,315,509 A | 2/1982 | Smit |
| 4,341,218 A | 7/1982 | U |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,823,808 A | 4/1989 | Clegg et al. |
| 4,846,836 A | 7/1989 | Reich |
| 4,878,905 A | 11/1989 | Blass |
| 4,905,693 A | 3/1990 | Ravo |
| 4,913,141 A | 4/1990 | Hillstead |
| 5,035,706 A | 7/1991 | Gianturco et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,104,399 A | 4/1992 | Lazarus |
| 5,135,516 A | 8/1992 | Sahatjian et al. |
| 5,152,756 A | 10/1992 | Quinn et al. |
| 5,176,617 A | 1/1993 | Fischell et al. |
| 5,190,561 A | 3/1993 | Graber |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A * | 4/1994 | Berry ................... 623/23.64 |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,423,851 A | 6/1995 | Samuels |
| 5,443,498 A | 8/1995 | Fontaine |
| 5,456,713 A | 10/1995 | Chuter |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,562,728 A | 10/1996 | Lazarus et al. |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,713 A | 9/1997 | Andersen et al. |
| 5,665,064 A | 9/1997 | Bodicky et al. |
| 5,669,932 A | 9/1997 | Fischell et al. |
| 5,690,642 A | 11/1997 | Osborne et al. |
| 5,693,084 A | 12/1997 | Chuter |
| 5,695,516 A | 12/1997 | Fischell et al. |
| 5,697,971 A | 12/1997 | Fischell et al. |
| 5,713,948 A | 2/1998 | Uflacker |
| 5,715,832 A | 2/1998 | Koblish et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,743,874 A | 4/1998 | Fischell et al. |
| 5,749,825 A | 5/1998 | Fischell et al. |
| 5,755,777 A | 5/1998 | Chuter |
| 5,759,174 A | 6/1998 | Fischell et al. |
| 5,776,186 A | 7/1998 | Uflacker |
| 5,792,144 A | 8/1998 | Fischell et al. |
| 5,792,172 A | 8/1998 | Fischell et al. |
| 5,800,456 A | 9/1998 | Maeda et al. |
| 5,800,526 A | 9/1998 | Anderson et al. |
| 5,820,584 A | 10/1998 | Crabb |
| 5,830,229 A | 11/1998 | Konya et al. |
| 5,840,009 A | 11/1998 | Fischell et al. |
| 5,843,164 A | 12/1998 | Frantzen et al. |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,910,145 A | 6/1999 | Fischell et al. |
| 5,913,895 A | 6/1999 | Burpee et al. |
| 5,919,233 A | 7/1999 | Knopf et al. |
| 5,925,063 A | 7/1999 | Khosravi |
| 5,962,620 A | 10/1999 | Reich et al. |
| 5,964,771 A | 10/1999 | Beyar et al. |
| 5,976,153 A | 11/1999 | Fischell et al. |
| 6,013,019 A | 1/2000 | Fischell et al. |
| 6,027,508 A | 2/2000 | Ren et al. |
| 6,027,526 A * | 2/2000 | Limon et al. ............... 623/1.15 |
| 6,035,856 A | 3/2000 | LaFontaine et al. |
| 6,074,673 A | 6/2000 | Guillen |
| 6,086,604 A | 7/2000 | Fischell et al. |
| 6,099,552 A | 8/2000 | Adams |
| 6,102,887 A | 8/2000 | Altman |
| 6,120,533 A | 9/2000 | Fischell |
| 6,146,323 A | 11/2000 | Fischell |
| 6,152,956 A | 11/2000 | Pierce |
| 6,179,868 B1 | 1/2001 | Burpee et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,241,738 B1 | 6/2001 | Dereume |
| 6,241,757 B1 | 6/2001 | An et al. |
| 6,251,064 B1 | 6/2001 | Silverman et al. |
| 6,251,132 B1 | 6/2001 | Ravenscroft et al. |
| 6,270,521 B1 | 8/2001 | Fischell et al. |
| 6,293,960 B1 | 9/2001 | Ken |
| 6,302,891 B1 | 10/2001 | Nadal |
| 6,302,917 B1 * | 10/2001 | Dua et al. ................. 623/23.68 |
| 6,315,708 B1 | 11/2001 | Salmon et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,356,782 B1 | 3/2002 | Sirimanne et al. |
| 6,375,660 B1 | 4/2002 | Fischell et al. |
| 6,387,114 B2 | 5/2002 | Adams |
| 6,401,718 B1 | 6/2002 | Johnson et al. |
| 6,406,792 B1 | 6/2002 | Briquet et al. |
| 6,428,558 B1 | 8/2002 | Jones et al. |
| 6,450,989 B2 | 9/2002 | Dubrul et al. |
| 6,458,074 B1 | 10/2002 | Matsui et al. |
| 6,485,409 B1 | 11/2002 | Voloshin et al. |
| 6,485,515 B2 | 11/2002 | Strecker |
| 6,508,833 B2 | 1/2003 | Pavcnik et al. |
| 6,520,985 B1 | 2/2003 | Burpee et al. |
| 6,524,335 B1 | 2/2003 | Hartley et al. |

| | | | | | | |
|---|---|---|---|---|---|---|
| 6,524,336 B1 | 2/2003 | Papazolgou et al. | 2003/0040808 A1 | 2/2003 | Stack et al. | |
| 6,530,951 B1 | 3/2003 | Bates et al. | 2003/0050684 A1 | 3/2003 | Abrams et al. | |
| 6,537,247 B2 | 3/2003 | Shannon | 2003/0055492 A1 | 3/2003 | Shaolian et al. | |
| 6,540,775 B1 | 4/2003 | Fischell et al. | 2003/0109892 A1 | 6/2003 | Deem et al. | |
| 6,540,789 B1 | 4/2003 | Silverman et al. | 2003/0109931 A1 * | 6/2003 | Geitz | 623/23.7 |
| 6,544,291 B2 | 4/2003 | Taylor | 2003/0109935 A1 | 6/2003 | Geitz | |
| 6,547,817 B1 | 4/2003 | Fischell et al. | 2003/0120265 A1 | 6/2003 | Deem et al. | |
| 6,558,400 B2 | 5/2003 | Deem et al. | 2003/0149467 A1 | 8/2003 | Linder et al. | |
| 6,558,429 B2 | 5/2003 | Taylor | 2003/0153927 A1 | 8/2003 | DiPoto et al. | |
| 6,565,597 B1 | 5/2003 | Fearnot et al. | 2003/0191476 A1 | 10/2003 | Smit | |
| 6,589,213 B2 | 7/2003 | Reydel | 2003/0199989 A1 | 10/2003 | Stack et al. | |
| 6,589,275 B1 | 7/2003 | Ivancev et al. | 2003/0199990 A1 | 10/2003 | Stack et al. | |
| 6,623,518 B2 | 9/2003 | Thompson et al. | 2003/0199991 A1 | 10/2003 | Stack et al. | |
| 6,635,069 B1 | 10/2003 | Teoh et al. | 2003/0208260 A1 | 11/2003 | Lau et al. | |
| 6,635,079 B2 | 10/2003 | Unsworth et al. | 2003/0216749 A1 | 11/2003 | Ishikawa et al. | |
| 6,645,239 B1 | 11/2003 | Park et al. | 2003/0233140 A1 | 12/2003 | Hartley et al. | |
| 6,652,555 B1 | 11/2003 | VanTassel et al. | 2004/0019388 A1 | 1/2004 | Starkebaum | |
| 6,656,194 B1 | 12/2003 | Gannoe et al. | 2004/0024386 A1 | 2/2004 | Deem et al. | |
| 6,669,722 B2 | 12/2003 | Chen et al. | 2004/0037865 A1 | 2/2004 | Miller | |
| 6,675,809 B2 | 1/2004 | Stack et al. | 2004/0039452 A1 | 2/2004 | Bessler | |
| 6,676,692 B2 | 1/2004 | Rabkin et al. | 2004/0044357 A1 | 3/2004 | Gannoe et al. | |
| 6,695,875 B2 | 2/2004 | Stelter et al. | 2004/0082963 A1 | 4/2004 | Gannoe et al. | |
| 6,699,263 B2 | 3/2004 | Cope | 2004/0092892 A1 | 5/2004 | Kagan et al. | |
| 6,699,278 B2 | 3/2004 | Fischell et al. | 2004/0092974 A1 | 5/2004 | Gannoe et al. | |
| 6,706,061 B1 | 3/2004 | Fischell et al. | 2004/0093065 A1 * | 5/2004 | Yachia et al. | 623/1.13 |
| 6,716,240 B2 | 4/2004 | Fischell et al. | 2004/0098079 A1 | 5/2004 | Hartley et al. | |
| 6,736,840 B2 | 5/2004 | Fischell et al. | 2004/0107004 A1 | 6/2004 | Levine et al. | |
| 6,740,121 B2 | 5/2004 | Geitz | 2004/0117031 A1 | 6/2004 | Stack et al. | |
| 6,755,869 B2 | 6/2004 | Geitz | 2004/0122452 A1 | 6/2004 | Deem et al. | |
| 6,773,440 B2 | 8/2004 | Gannoe et al. | 2004/0122453 A1 | 6/2004 | Deem et al. | |
| 6,776,791 B1 | 8/2004 | Stallings et al. | 2004/0122470 A1 | 6/2004 | Deem et al. | |
| 6,802,868 B2 | 10/2004 | Silverman et al. | 2004/0133147 A1 | 7/2004 | Woo | |
| 6,821,291 B2 | 11/2004 | Bolea et al. | 2004/0136971 A1 | 7/2004 | Scharp et al. | |
| 6,845,776 B2 | 1/2005 | Stack et al. | 2004/0138525 A1 | 7/2004 | Saadat et al. | |
| 6,936,065 B2 | 8/2005 | Khan et al. | 2004/0138529 A1 | 7/2004 | Wiltshire et al. | |
| 7,011,673 B2 | 3/2006 | Fischell et al. | 2004/0138760 A1 | 7/2004 | Schurr | |
| 7,025,791 B2 | 4/2006 | Levine et al. | 2004/0138761 A1 | 7/2004 | Stack et al. | |
| 7,033,384 B2 | 4/2006 | Gannoe et al. | 2004/0143342 A1 | 7/2004 | Stack et al. | |
| 7,037,327 B2 | 5/2006 | Salmon et al. | 2004/0148034 A1 | 7/2004 | Kagan et al. | |
| 7,037,344 B2 | 5/2006 | Kagan et al. | 2004/0153167 A1 | 8/2004 | Stack et al. | |
| 7,054,690 B2 | 5/2006 | Imran | 2004/0158229 A1 | 8/2004 | Quinn | |
| 7,122,058 B2 * | 10/2006 | Levine et al. ............ 623/23.65 | 2004/0158331 A1 | 8/2004 | Stack et al. | |
| 7,146,984 B2 | 12/2006 | Stack et al. | 2004/0172063 A1 | 9/2004 | Li et al. | |
| 7,152,607 B2 | 12/2006 | Stack et al. | 2004/0172088 A1 | 9/2004 | Knudson et al. | |
| 7,160,312 B2 | 1/2007 | Saadat | 2004/0172141 A1 | 9/2004 | Stack et al. | |
| 7,211,114 B2 | 5/2007 | Bessler | 2004/0172142 A1 * | 9/2004 | Stack et al. | 623/23.65 |
| 7,220,237 B2 | 5/2007 | Gannoe et al. | 2004/0172143 A1 | 9/2004 | Geitz | |
| 7,220,284 B2 | 5/2007 | Kagan et al. | 2004/0181242 A1 | 9/2004 | Stack et al. | |
| 7,267,694 B2 * | 9/2007 | Levine et al. ............. 623/23.7 | 2004/0193093 A1 | 9/2004 | Desmond, III | |
| 7,314,489 B2 | 1/2008 | McKenna et al. | 2004/0204768 A1 | 10/2004 | Geitz et al. | |
| 7,329,285 B2 | 2/2008 | Levine et al. | 2004/0210243 A1 | 10/2004 | Gannoe et al. | |
| 7,338,520 B2 | 3/2008 | Bailey et al. | 2004/0220682 A1 | 11/2004 | Levine et al. | |
| 7,347,875 B2 | 3/2008 | Levine et al. | 2004/0236401 A1 | 11/2004 | Shin et al. | |
| 7,354,454 B2 | 4/2008 | Stack et al. | 2004/0249362 A1 | 12/2004 | Levine et al. | |
| 7,476,256 B2 | 1/2009 | Meade et al. | 2005/0004681 A1 | 1/2005 | Stack et al. | |
| 2001/0020190 A1 | 9/2001 | Taylor | 2005/0043601 A1 | 2/2005 | Kilcoyne et al. | |
| 2002/0032487 A1 | 3/2002 | Dua et al. | 2005/0043817 A1 | 2/2005 | McKenna et al. | |
| 2002/0065545 A1 | 5/2002 | Leonhardt et al. | 2005/0049718 A1 | 3/2005 | Dann et al. | |
| 2002/0091439 A1 | 7/2002 | Baker et al. | 2005/0055039 A1 | 3/2005 | Burnett et al. | |
| 2002/0099439 A1 | 7/2002 | Schwartz et al. | 2005/0075622 A1 | 4/2005 | Levine et al. | |
| 2002/0107565 A1 | 8/2002 | Greenhalgh | 2005/0080395 A1 | 4/2005 | Levine et al. | |
| 2002/0120277 A1 | 8/2002 | Hauschild et al. | 2005/0080431 A1 | 4/2005 | Levine et al. | |
| 2002/0143387 A1 | 10/2002 | Soetikno et al. | 2005/0080491 A1 | 4/2005 | Levine et al. | |
| 2002/0147489 A1 | 10/2002 | Hong et al. | 2005/0085787 A1 | 4/2005 | Laufer | |
| 2002/0151953 A1 | 10/2002 | Chobotov et al. | 2005/0085923 A1 | 4/2005 | Levine et al. | |
| 2002/0177890 A1 | 11/2002 | Lenker | 2005/0090873 A1 | 4/2005 | Imran | |
| 2002/0183768 A1 | 12/2002 | Deem et al. | 2005/0096750 A1 | 5/2005 | Kagan et al. | |
| 2002/0183786 A1 | 12/2002 | Girton | 2005/0125020 A1 | 6/2005 | Meade et al. | |
| 2002/0188344 A1 | 12/2002 | Bolea et al. | 2005/0125075 A1 | 6/2005 | Meade et al. | |
| 2002/0193828 A1 | 12/2002 | Griffin et al. | 2005/0149114 A1 | 7/2005 | Cartledge et al. | |
| 2003/0009236 A1 | 1/2003 | Godin | 2005/0171556 A1 | 8/2005 | Murphy | |
| 2003/0032941 A1 | 2/2003 | Boyle et al. | 2005/0182483 A1 | 8/2005 | Osborne et al. | |
| 2003/0040804 A1 | 2/2003 | Stack et al. | 2005/0192614 A1 | 9/2005 | Binmoeller | |

| | | | |
|---|---|---|---|
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0256587 A1 | 11/2005 | Egan |
| 2005/0267533 A1 | 12/2005 | Gertner |
| 2006/0009858 A1 | 1/2006 | Levine et al. |
| 2006/0106332 A1 | 5/2006 | Knudson et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2007/0005147 A1 | 1/2007 | Levine et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1 | 4/2007 | Levine et al. |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0208357 A1 | 8/2008 | Melanson et al. |
| 2008/0223476 A1 | 9/2008 | Stinson |
| 2008/0234834 A1 | 9/2008 | Meade et al. |

FOREIGN PATENT DOCUMENTS

| | | |
|---|---|---|
| EP | 0 480 667 B1 | 4/1992 |
| EP | 0278937 B1 | 10/1993 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| EP | 1 504 778 A2 | 2/2005 |
| EP | 1 504 778 A3 | 2/2005 |
| JP | 04212348 | 8/1992 |
| WO | WO 92/06734 A1 | 4/1992 |
| WO | WO 95/05132 | 2/1995 |
| WO | WO 97/03624 A1 | 2/1997 |
| WO | WO 98/22045 A | 5/1998 |
| WO | WO 99/23953 A | 5/1999 |
| WO | WO 99/44536 A | 9/1999 |
| WO | WO 00/12027 | 3/2000 |
| WO | WO 00/28922 A1 | 5/2000 |
| WO | WO 00/32137 | 6/2000 |
| WO | WO 00/42945 A1 | 7/2000 |
| WO | WO 00/42949 | 7/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 A1 | 12/2005 |
| WO | WO 2006/016894 A1 | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO 2006/088578 A1 | 8/2006 |
| WO | WO 2006/102012 A1 | 9/2006 |
| WO | WO 2006/133311 A2 | 12/2006 |

OTHER PUBLICATIONS

Parodi, J.C., M.D., "Endovascular Repair of Abdominal Aortic Aneurysms," *Advances in Vascular Surgery*, vol. 1, pp. 85-105 (1993).

Yates III, M. R., et al., "Palliation of Malignant Gastric and Small Intestinal Strictures With Self-Expandable Metal Stents," *Endoscopy* 30:266-272 (1998).

Bethge, N., et al., "Human tissue responses to metal stents implanted in vivo for the palliation of malignant stenoses," *Gastrointestinal Endoscopy* 43(6):596-602 (1996).

Binkert, C. A., et al., "Benign and Malignant Stenoses of the Stomach and Duodenum: Treatment with Self-expanding Metallic Endoprostheses," *Radiology* 199(2):335-338 (1996).

Cwikiel, W., et al., "Self-expanding Stent in the Treatment of Benign Esophageal Strictures: Experimental Study in Pigs and Presentation of Clinical Cases," *Radiology* 187(3):667-671 (1993).

Dolan, K. et al., "Treating Diabetes in the Morbidly Obese by Laproscopic Gastric Band," *Obesity Surgery*, vol. 13, pp. 439-443 (2003).

Park, B.P. et al., Malignant Obstruction of Gastric Outlet and Duodenum: Palliation with Flexible Covered Metallic Stents, *Radiology* 219(3):679-683 (2001).

Dormann, A.J. et al., "Self-expanding metallic stents for continous dilatation of benign stenosis in gastrointestinal tract—first results of long-term follow-up in interim stent application in pyloric and colonic obstructions," *Z Gastroenteral* 39:957-960 (2001).

Pories, W.J., "Why Does the Gastric Bypass Control Type 2 Diabetes Mellitus?" *Obesity Surgery*, 2:303-313 (1992).

Pories, W.J., et al., "Etiology of Type II Diabetes Mellitus: Role of the Foregut," *World J. Surg.*, 25:527-531 (2001).

Rubino, F., et al., "Potential of Surgery for Curing Type 2 Diabetes Mellitus," *Annals of Surgery* 236(5): 554-559 (2002).

Sandha, G. S. and Marcon, N. E., "Expandable Metal Stents For Benign Esophageal Obstruction," Gastrointestinal Endoscopy Clinics of North America 9:(3)437-446 (1999).

Feretis, C., et al., "Palliation of Malignant Gastric Outlet Obstruction with Self-Expanding Metal Stents," Endoscopy 28:225-228 (1996).

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11 (2004).

CHOOSTENT™, Covered Esophageal Stent, Instructions, Retrieved from the Internet (http://mitech.co.kr/uploads/images/282/use_guide_esophachoo_english.pdf) on Jul. 26, 2005.

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul.-Aug. 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

\* cited by examiner

ATRAUMATIC GASTROINTESTINAL ANCHOR

RELATED APPLICATION

This application claims the benefit of U.S. Provisional Application No. 60/611,038, filed on Sep. 17, 2004. The entire teachings of the above application are incorporated herein by reference.

BACKGROUND OF THE INVENTION

Anchors are used in the treatment of patients to secure devices at a desired location within a natural bodily lumen. For example, anchors can be used to secure tubes within the digestive tract, such as intestinal sleeves. For example intestinal sleeves anchored within the gastrointestinal tract are described in U.S. application Ser. No. 10/339,786 filed on Jan. 9, 2003, claiming priority to U.S. Provisional Application No. 60/430,321 filed on Dec. 2, 2002; Ser. No. 10/858,852 filed on Jun. 16, 2004, claiming priority to U.S. Provisional Application Nos. 60/528,084 filed on Dec. 9, 2003 and 60/544,527 filed on Dec. 14, 2004, incorporated herein by reference in their entirety.

SUMMARY OF THE INVENTION

This invention is generally related to articles and methods for anchoring within a natural bodily lumen, and particularly to articles and methods for anchoring atraumatically.

Unfortunately, stiff anchors can traumatize surrounding tissue. This is particularly true in biological applications in which the anchor operates against softer bodily tissues. A stiff anchor may be used within a bodily lumen, such as the intestine to prevent a medical device (e.g., a sleeve) from migrating therein. In some applications, the anchor includes barbs adapted to pierce a portion of the lumen. For the barbs to be effective, at least some of them must engage the tissue at all times. To accomplish this continued engagement, anchors provide a sufficient securing force adapted to maintain the barbs within the tissue. As this securing force can be substantial, tissue damage at the proximal and distal ends of the anchor are likely to occur.

To anchor within a lumen, anchors generally apply at least some outward force directed toward the inner walls of the lumen. Depending upon the application, the anchoring force can vary from a minimal force (e.g., to hold hooks in position) to a more substantial force (e.g., forming an interference fit). In biological applications the inner walls of a lumen typically contain tissue that is soft and particularly vulnerable to irritation. Thus, in these applications a greater force increases the risk that the anchor will lead to trauma by way of irritation or even tissue damage.

Such irritation and tissue damage are particular concerns for anchors adapted for use within the intestine. Unfortunately, the high mobility of the intestine and the nature of the forces acting on material within the intestine (i.e., peristalsis) complicate anchoring there. Thus, a more substantial force is typically required to secure an intestinal anchor in place.

The present invention relates to an intraluminal anchor adapted for implanting within a natural bodily lumen. The intraluminal anchor includes an elongated anchor having a longitudinal axis adapted for alignment with the natural bodily lumen. The elongated anchor includes a primary anchoring region adapted to expand against the lumen. The anchor also includes secondary anchoring regions disposed along either side of the primary anchoring region. The secondary anchoring regions are also adapted to expand against the lumen with the primary anchoring region expanding to a greater extent than the outer ends of the secondary anchoring regions.

The intraluminal anchor also includes an elongated anchoring member that, when implanted, provides at least two different radial forces at respective positions along its length. These different radial forces act differently upon respective portions of the natural bodily lumen when the device is implanted therein. Namely, at least one of the radial forces is primarily a securing force adapted to anchor within the natural bodily lumen. The other radial force is a transitional force adapted to mitigate damage to the natural bodily lumen. Further, when implanted, the intraluminal anchor defines an interior lumen allowing for continued functioning of the natural bodily lumen.

The elongated anchoring member can include plural anchoring elements each providing a respective radial force, at least one of the elements providing a different radial force from the others. By positioning each of the plural anchoring elements at a respective position along the length of the intraluminal anchor, the respective radial forces, including the different radial force, are disposed at different lengths along the natural bodily lumen.

The different radial force can be provided by forming one or more of the anchoring elements from a different material than the other anchoring elements. Preferably, the different materials provide different compliance values that produce different radial forces when implanted. Alternatively, or in addition, the different anchoring elements can be formed from the same material but in a different configuration, such as its shape or thickness.

At least some of the anchoring elements can be coupled to each other. For example, in some embodiments at least one joining member is coupled between adjacent anchoring elements, the joining member coupling two or more anchoring elements together.

In some embodiments having plural anchoring elements, at least one of the anchoring elements can be formed from an elongated wire. The elongated wire can be formed in any suitable shape, such as a helix or an oscillating (i.e., wave-shaped) pattern. The wave-shaped pattern distributes the respective radial force over the length of the anchoring element while also improving performance of the anchoring element's respective radial expansion and contraction.

To further enhance its anchoring performance, the intraluminal anchor can include at least one external barb adapted to penetrate tissue of the natural bodily lumen. The external barb is located at a predetermined position along the length of the intraluminal anchor, the corresponding radial force acting to press the barb into the tissue. For example, in a multi-anchoring element embodiment, the at least one external barb can be coupled to one of the anchoring elements. The force of the coupled anchoring element then acts to hold the barb within the tissue.

In some embodiments, the external barb can be a bi-directional barb. Bi-directional barbs are particularly well suited for applications in which the intraluminal anchor is subjected to external forces acting in either direction along the natural bodily lumen. Generally, the bi-directional barb includes a first barb segment adapted to oppose proximal movement and a second barb segment adapted to oppose distal movement. Such barbs are well suited to gastrointestinal applications in which the device is subjected to the substantial axial forces of peristalsis.

Preferably, the anchor is radially collapsible for endoscopic insertion. The intraluminal anchor can also include a drawstring to facilitate repositioning and/or removal. The drawstring, for example, can be provided at a proximal end of the device and be adapted for engagement by a removal device, such as a hook. The drawstring, when engaged, can be pushed or pulled by the removal device, in opposition to the stationary intraluminal anchor, to at least partially collapse at least part of the intraluminal anchor. With a reduced diameter, the device can be removed through, or repositioned within, the natural bodily lumen. In some embodiments, at least a portion of the device is drawn into a retrieval hood, sheath, or overtube prior to removal.

In some embodiments, the intraluminal anchor is coupled to an elongated tube at a proximal end of the tube, the tube being adapted to extend distally within the natural bodily lumen. The elongated anchoring element can be coupled to the elongated tube in any of a number of different ways. For example, the anchoring element can be mechanically fastened using sutures, staples, or the like. Alternatively or in addition, the anchoring element can be bonded to the tube, using a chemical adhesive and/or heat welding. In some embodiments the tube is thin-walled, and flexible. For example, the tube can be formed as a sleeve having extremely thin and floppy walls, the sleeve tending to collapse upon itself. The anchoring element can secured between at least two overlapping layers of the sleeve. The overlapping layers can then be attached to each other using any available fastening technique including bonding together at least a portion of the overlapping layers of the sleeve.

In other embodiments, the elongated anchoring element can be formed from a homogeneous hollow tube. The thickness of the tube can be altered (i.e., tapered) along the length of the tube, such that different portions of the tube provide different spring forces. When implanted within a naturally bodily lumen, the tapered tube provides different forces along its length and therefore different forces along the bodily lumen according to the thickness of the tube. In some embodiments, the tapered tube can be further modified using known techniques (e.g., laser cutting) to promote radial expansion and contraction of the device.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

An anchor is adapted for anchoring within a natural bodily lumen while allowing continued functionality of the lumen and providing minimal trauma to the surrounding anatomy. Such an anchor provides a securing force acting upon the surrounding anatomy to hold the anchor fast, even in the presence of anticipated biological forces. For example, the securing force would hold a gastrointestinal anchor in position even in the presence of peristalsis. Anchoring against such forces, however, may require substantial securing force that could otherwise damage the surrounding tissue.

Figure 1A:
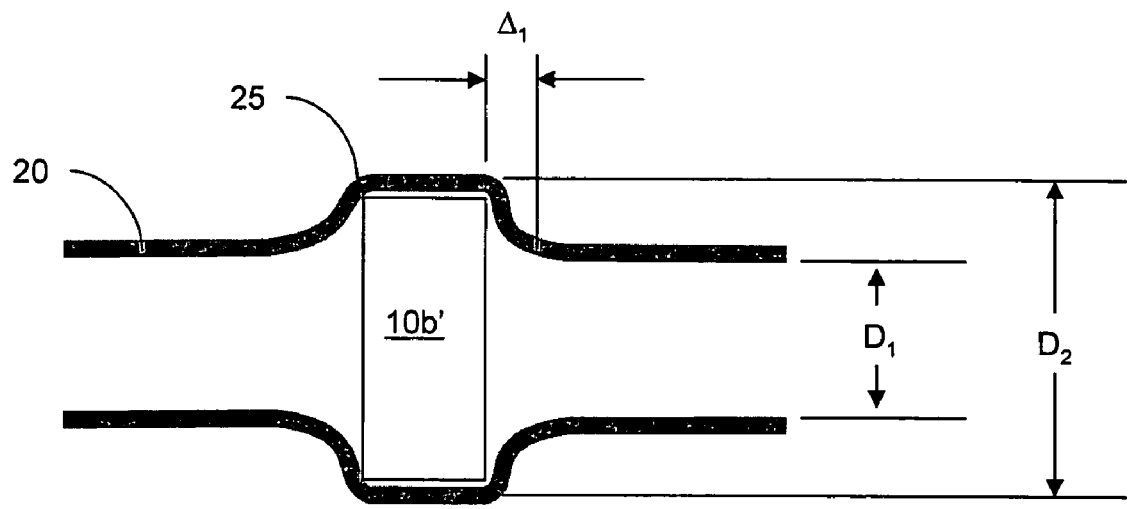
FIG. 1A is a schematic diagram illustrating a prior art intraluminal anchor implanted within a natural bodily lumen.

A cross-section of a natural bodily lumen 20 including an anchor 10b' is illustrated in FIG. 1A. Generally, the lumen defines a natural diameter, $D_1$, that may vary over time. The anchor provides a radially-outward securing force directed against the luminal walls. Depending upon the structure of the anchor 10b' and the compliance of the luminal walls, the anchor 10b' when implanted can increase the intraluminal diameter (i.e., $D_2$) as shown. The sharp transition from the anchored region to the unsupported adjacent region applies a strain to the tissue, particularly at the ends of the anchor 25. As shown, tissue stretching can occur over a first distance $\Delta_1$. Such a strain can lead to irritation of the tissue or even damage over time.

Figure 1B:
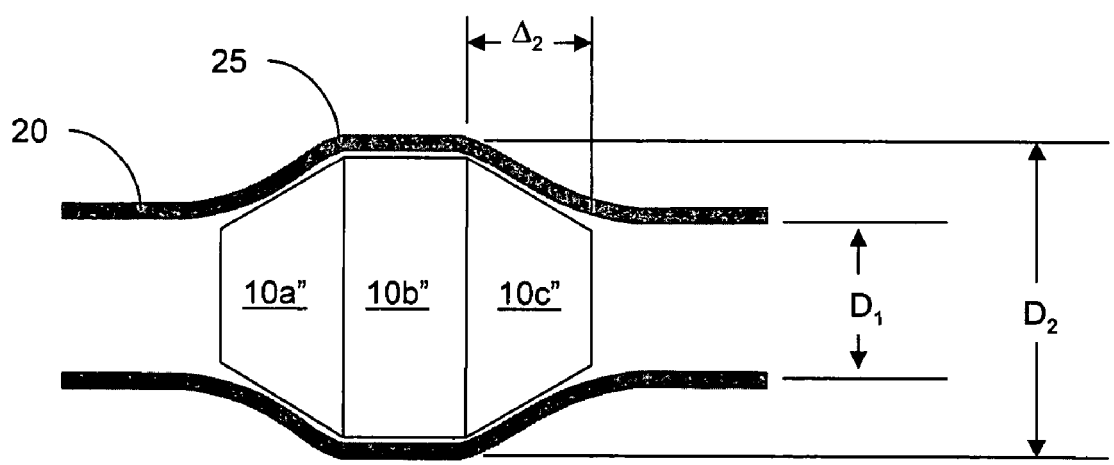
FIG. 1B is a schematic diagram illustrating an embodiment of an intraluminal anchor according to the principles of the invention implanted within a natural bodily lumen.

To offset the possibility of damage due to the securing force, the anchor also provides a transitional force that is different from the securing force and acts upon an adjacent region of the surrounding anatomy. As shown in FIG. 1B, an anchor 10b'' providing a securing force is surrounded on either side by another anchoring element 10a'', 10c'' providing a lesser, transitional force. The transitional force allows for a more gradual decrease in anchoring force from a central region along the length of the anchor and thus less trauma. Thus, the transition from an expanded diameter $D_2$ to the natural luminal diameter $D_1$ occurs over a second distance $\Delta_2$, that is greater than first distance $\Delta_1$. By transitioning from unsupported tissue to anchored tissue using a softer anchoring element, the strain to the tissue is reduced, thereby reducing the likelihood of tissue irrigation and damage.

By applying different forces at different lengths along the natural bodily lumen, the securing force can be applied, or focused where needed, while the transitional force can distribute the pressure loading to the surrounding anatomy. In particular, the transitional force is a lesser force than the securing force, providing a gradual transition from the luminal region subjected to the securing force, to adjacent, unsupported luminal regions. Preferably, the anchor can be used in combination with another instrument, such as a feeding tube or a gastrointestinal sleeve, to secure the instrument at a predetermined location within the bodily lumen.

Figure 2:
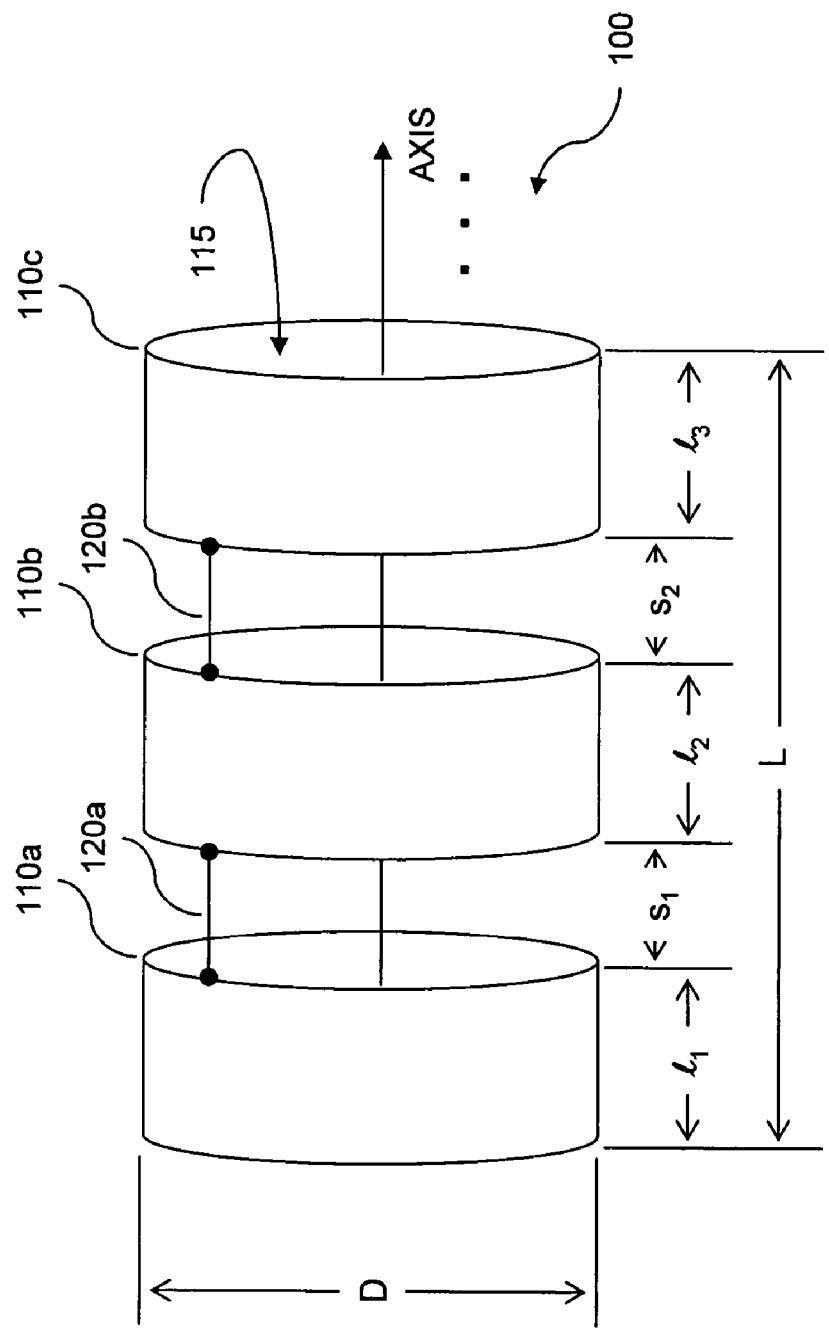
FIG. 2 is a schematic diagram illustrating an embodiment of an intraluminal anchor.

FIG. 2 schematically illustrates an exemplary embodiment of an intraluminal anchor 100. The anchor 100 has an overall axial-length 'L' measured length-wise with respect to the lumen and defines an interior channel 115 configured to allow continued operation of the lumen when implanted therein. For example, the anchor 100 can have a generally cylindrical shape, having a length 'L', a diameter 'D', and defining an interior channel 115. When implanted, the anchor provides a radially-outward spring force directed against the adjacent walls of the natural bodily lumen (i.e., the anchor includes an annular, radial spring providing a force corresponding to a displacement of the spring along its radius). The radial force includes a securing force, sufficient to secure the anchor 100 in place under anticipated bodily forces. In particular, the outward radial force is varied along the length of the anchor to provide a transitional force, reducing the likelihood of damage to surrounding tissue. When implanted within a natural bodily lumen, the anchor provides a transition along the lumen from soft tissue, to a low compliance region (i.e., transitional force), to a higher compliance region (i.e., securing force), again to a low compliance region, and ultimately back to unsupported, soft tissue.

Generally, the anchor includes a spring providing the desired securing force. The force produced by the spring is defined by an associated spring rate relating to its compliance or stiffness. The spring rate can be determined by one or more anchor features including its type of material, material thickness, dimensions, and shape. As a radial spring, a greater force results from a greater radial displacement. For intraluminal applications, such a radial spring preferably has a relaxed diameter (i.e., no load diameter) that is greater than the largest anticipated intraluminal diameter. Thus, the implanted anchor is always subjected to a compressive force causing radial compression and leading to an opposing securing force. Compliant anchors are described in U.S. application Ser. No. 11/147,992 filed on Jun. 8, 2005, incorporated herein by reference in its entirety.

In many applications the anchor remains sufficiently compliant, when implanted, to conform to the walls of the lumen over a full range of motion. For example, an anchor implanted within the proximal duodenum of an adult human may experience intraluminal diameter variations from about 25-millimeters or less, to greater than 50-millimeters.

As suggested by FIG. 2, the anchor 100 can provide a varied force by using plural anchoring elements. For example, the anchor 100 can include three or more different anchoring elements 110a, 110b and 110c (generally 110), as shown. Each of the anchoring elements 110a, 110b and 110c can be annular, as shown, and occupy a respective axial sub-length '$l_1$,' '$l_2$,' and '$l_3$.' Further, each of the anchoring elements 110 can be separated from its neighboring anchoring element by a respective distance '$s_1$,' '$s_2$.' In some embodiments, the one or more of the distances can be negative, suggesting that the elements overlap. The overall length of the anchor 100 is determined as the sum of the sub-lengths of the anchoring elements and any distances provided therebetween. Each of the annular anchoring elements 110 can be sized and shaped to conform to the walls of the surrounding lumen with its opening collinearly aligned with a luminal axis.

In some embodiments, the anchoring elements 110 are coupled together using a respective cross-linking, or joining member 120a, 120b (generally 120), as shown. The joining member 120 can be a rigid member or strut, such as a wire or rod. Use of rigid struts can reduce or substantially eliminate axial compression of the device. Alternatively or in addition, the joining member 120 can be flexible, such as a wire, tape, or thread (e.g., a suture). Such flexible members can permit axial compression but not expansion, so the length can be less than or equal to a maximum length. If axial compression and expansion is desired, the joining members 120 can include elastic elements. Such flexibility can be beneficial to both patient comfort and anchoring effectiveness. In some embodiments, the joining members 120 are formed integrally to the anchoring elements 110 themselves.

Figure 3:
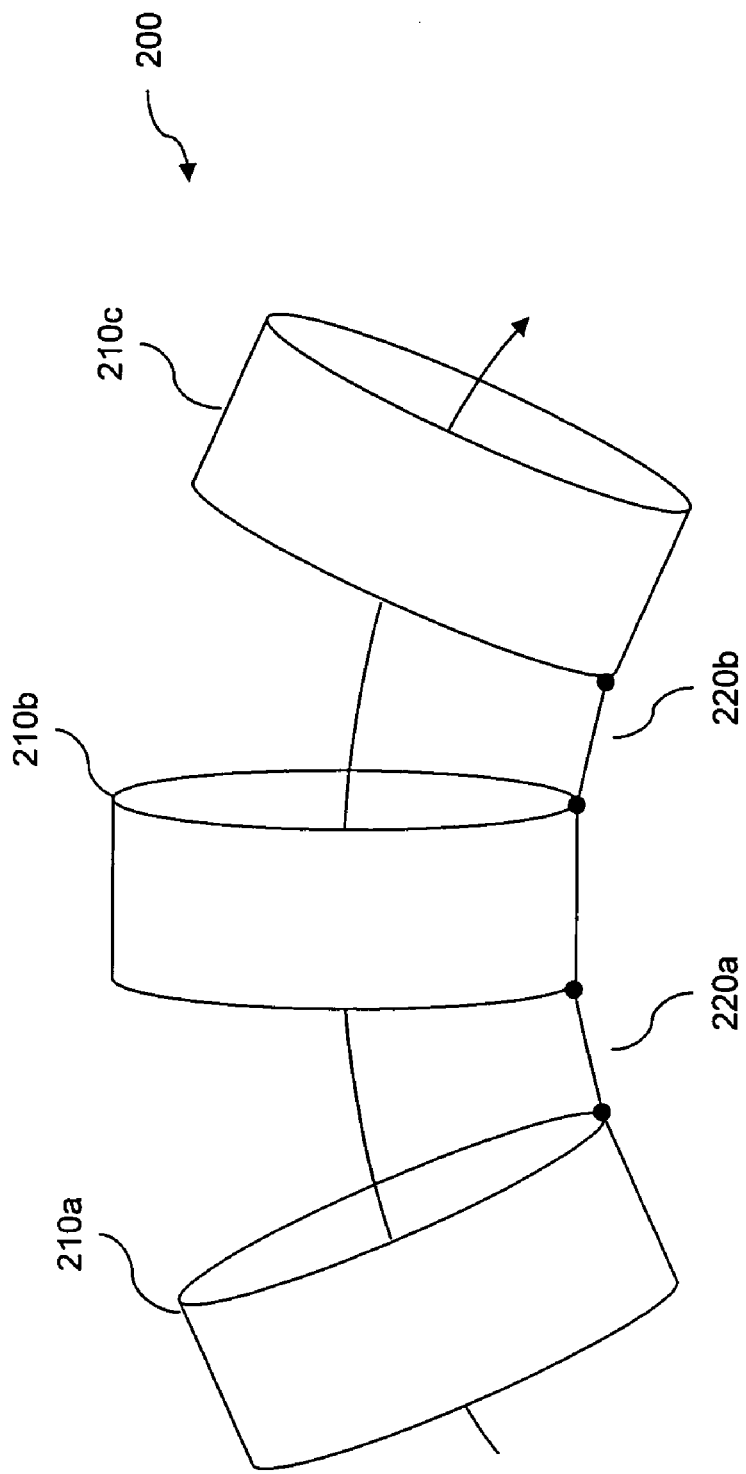
FIG. 3 is a schematic diagram illustrating an embodiment of a bendable, intraluminal anchor.

An embodiment of a flexible elongated anchor 200 is illustrated in FIG. 3. The elongated anchor 200 can include more than one anchoring element 210a, 210b, 210c, each capable of independent movement with respect to the other elements. The anchor 200 may include joining members 220a, 220b, but they are selected and positioned to allow a desired flexibility. For example, rigid joining members can be aligned along one side of the anchor 200, allowing the anchor to bend towards that side.

Figure 4A:
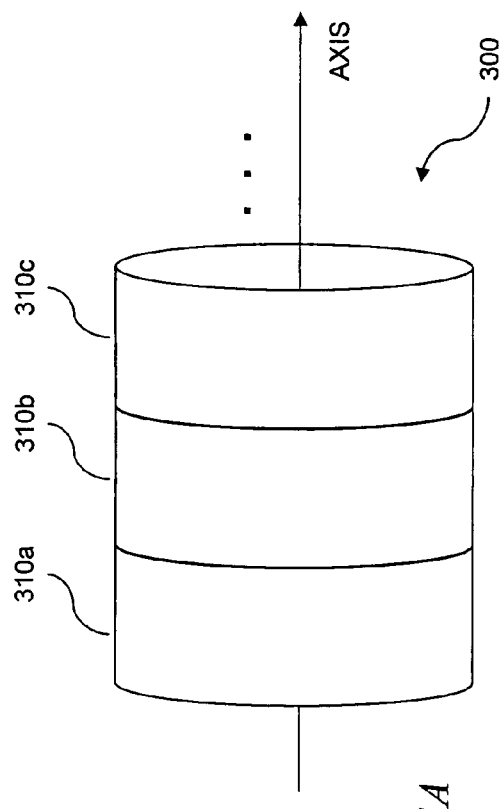
FIG. 4A is a schematic diagram illustrating an alternative embodiment of the intraluminal anchor shown in FIG. 1.
Figure 4B:
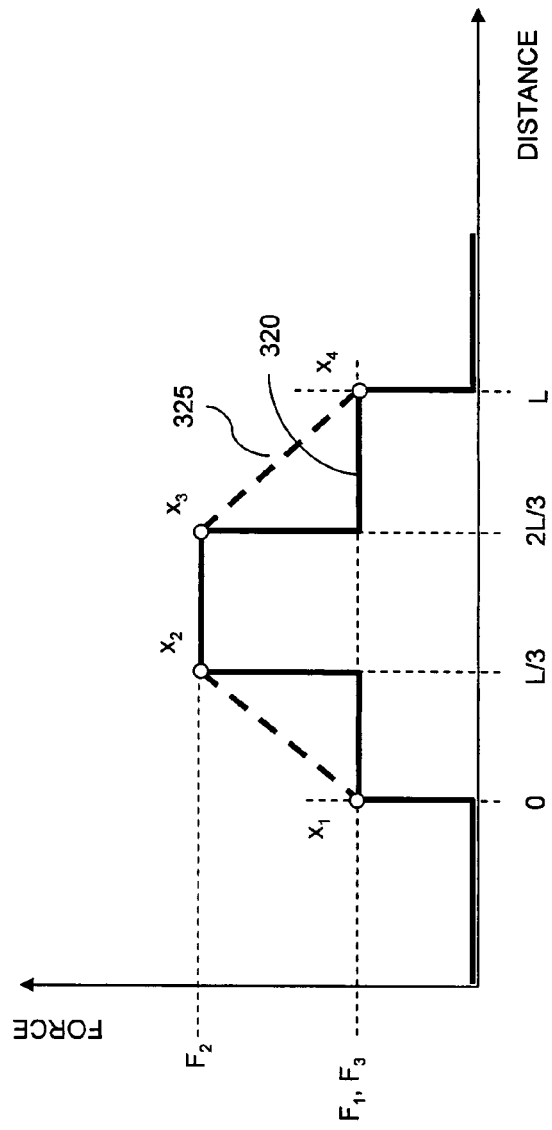
FIG. 4B is an exemplary radial-force profile for the intraluminal anchor of FIG. 4A.

An alternative embodiment of an intraluminal anchor 300 is illustrated in FIG. 4A. The anchor 300 includes multiple anchoring elements 310a, 310b, 310c in a collinear arrangement with adjacent elements 310 abutting. A corresponding force-versus-distance graph for the anchor 300 is illustrated in FIG. 4B. In particular, the graph illustrates the different radially-outward forces provided by each of the anchoring elements 310 (FIG. 4A) versus its respective distance as measured along a central axis of the anchor 300. As shown for the exemplary embodiment of FIG. 4A, the greater radial force is provided by the central element 310b, having a representative force of $F_2$. The corresponding force can be substantially constant across the axial length subtended by the second anchoring element 310b (i.e., from L/3 to 2 L/3, assuming all three elements are of equal length L/3). Similarly, forces $F_1$ and $F_3$ provided by the adjacent first and third anchoring elements 310a, 310c are lesser forces, as shown in the graph (e.g., at region 320). The greater force $F_2$ corresponds to a securing force to hold the anchor in place when implanted; whereas, the lesser forces $F_1$ and $F_3$ correspond to transitional forces lessening the likelihood of damage to surrounding tissue.

In some embodiments, however, the structure of the anchoring elements 310 allows the elements to provide different forces along their respective sub-lengths. As the anchoring elements 310 are radial springs, they have an associated spring constant. The radial force provided by the anchoring element 310 is thus a result of the spring constant and the amount of radial compression. Anchoring element configurations that allow for varied compression along the anchor sub-length will lead to a corresponding varied radial force. For example, if the outer anchoring elements 310a, 310c are each coupled at one end to the central anchoring element 310b, they may have a different diameter on each end. As the central anchoring element 310b is stiffer, it may have a greater diameter than a less stiff element. In general, there is no limit to the number of anchoring elements that can be provided or to the particular stiffness profile desired.

The securing force produced by the anchor can include a radial component directed outward and pressing against the walls of the surrounding lumen. The securing force can also include an axial component provided by a barb. The magnitude of the securing force preferably depends on the intended application being selected to sufficiently secure the anchor without being excessive. Limiting the maximum force is important as substantial forces acting against the luminal walls are more apt to traumatize the surrounding tissue.

In some embodiments, the radially-outward force of an anchor is varied by varying the stiffness (or compliance) of the anchor along its length. Such a feature provides for greater flexibility in tailoring the anchor to its intended delivery location. For example, the thickness of the anchor member can be varied to control the desired stiffness, such that a portion of the anchor is relatively stiff, whereas another portion of the anchor is relatively soft. In this manner, the stiffer portion of the anchor can be used to distend that portion of the bodily lumen within which it is implanted. To reduce irritation, the stiffness is then reduced towards the proximal and distal ends of the anchor to reduce any trauma to the tissue of the bodily lumen.

Figure 5A:
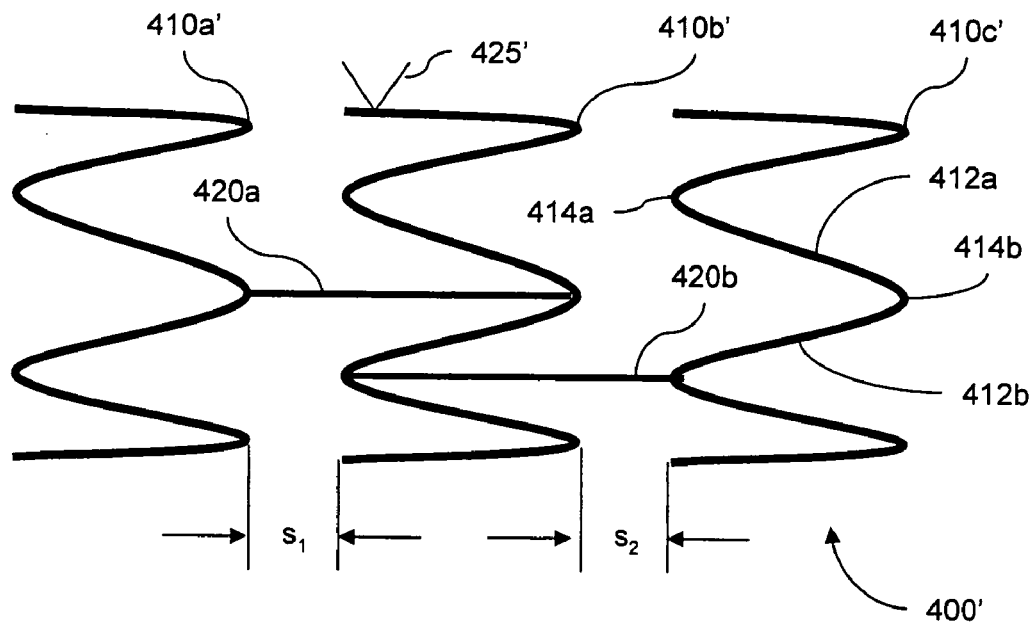
FIGS. 5A and 5B are schematic diagrams illustrating alternative embodiments of the intraluminal anchor shown in FIG. 2 having cross-linking members.

For example, a side view of a flexible intraluminal anchor 400' is illustrated in FIG. 5A. By using different anchoring elements 410a', 410b', 410c', interconnected by joining members 420a', 420b' (generally 420') as shown, the anchor 400' is allowed to flex and bend. The joining members 420' are not necessary for embodiments in which the elements 410 are each coupled to the same tube or sleeve. The anchoring elements 410' are each formed from a respective continuous wire fashioned into the oscillating, wave-shaped pattern shown. Viewed along an axis (not shown), the anchor 400' would appear as an open circle or hoop. Wave-shaped anchors and related matters are described in U.S. application Ser. No. 10/858,852 filed on Jun. 1, 2004 and claiming priority to U.S. Provisional Application Nos. 60/528,084 filed on Dec. 9, 2003 and 60/544,527 filed on Dec. 13, 2004. The entire teachings of these applications are incorporated herein by reference in their entirety.

In one embodiment, the central anchoring element 410b' is formed from a relatively thick wire, such as a 0.023 inch diameter Nitinol wire. The additional anchoring elements 410a', 410c' are formed from a thinner wire, such as a 0.014 inch diameter Nitinol wire. Using wires formed from the same material, the thicker wire results in a greater stiffness than the thinner wire. Thus, the central anchoring 410b' element provides a greater radially-outward force when compressed than either of the two surrounding anchoring elements 410a', 410c'. The spring rate can also be varied by altering the axial length of a wave-shaped anchoring element, shorter elements being stiffer than longer ones. Also, the spring rate can be varied by altering the number of oscillations for a give anchoring element, elements with more oscillations being stiffer.

The wires can be formed from any suitable material, such as metals, metal alloys (e.g., stainless steel and Nitinol), and/ or synthetic materials (e.g., plastic). Preferably, the material is bio-compatible, although it is possible to use non bio-compatible material that is coated or encapsulated in a bio-compatible material. Anchoring can be accomplished using an interference fit between the intraluminal anchor and the inner walls of the lumen. Alternatively or in addition, anchoring can be accomplished using other means including sutures, staples, surgical adhesives and/or barbs or hooks. In the exemplary embodiment, at least one external barb 425' is be attached to the central anchoring element 410b'. When implanted, the barb 425' is held in place within muscular tissue by the stiffness and corresponding radially-outward force of the 0.023 inch diameter wire. The central anchor element 410b provides a substantial force to keep the barb 425' inserted into the surrounding tissue. Without the first and third anchoring elements 410a', 410c', the securing force provided by the middle anchoring element 410b' could lead to tissue irritation or even damage at the ends of the element 410b'.

The anchoring elements described above can be formed into any number of different shapes. In some embodiments, each of the anchoring elements is formed in a wave shape. Thus, a linear element (i.e., a wire) is contoured into an oscillating manner along a cylindrical surface at a distance (i.e., a radius) from a central axis. Such a wire form can be shaped on a cylindrical mandrel. The two ends of the wire are joined together (e.g., crimped, soldered, or chemically or thermally bonded) forming a continuous structure. An anchoring element thus formed provides a relatively small surface area in contact with the natural bodily lumen, while allowing the anchor to provide a relatively large diameter (e.g., 25 to 50 or more millimeters for gastrointestinal applications). The oscillations result in relatively straight segments 412a, 412b (generally 412) interconnected at nodes 414a, 414b (generally 414). When compressed in a radial direction, the nodes 414 flex allowing the relatively straight segments 412 to become more aligned with respect to each other. Thus, the diameter of the anchor 400' can be reduced substantially to allow for its insertion and/or removal through a relatively small diameter. For example, in some intestinal applications, a 50-millimeter diameter device is adapted to be inserted through a 12-millimeter diameter catheter. When released, the anchor 400' expands with spring force against the walls of the bodily lumen.

Figure 5B:
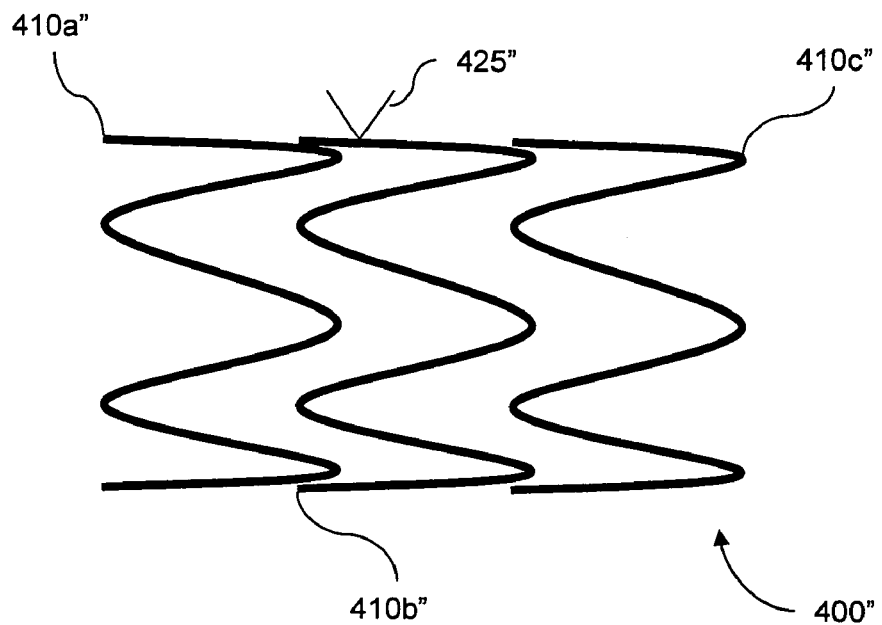

The anchoring elements 410a', 410b', 410c' may be separated by respective distances $s_1$, $s_2$ as shown, or one or more of the elements may be adjacent or even overlapping. An alternative embodiment of a wave-shaped wire anchor 400" is illustrated in FIG. 5B. The anchoring 400" also includes multiple anchoring elements 410a", 410b", 410c" that may or may not be interconnected by joining members 420a", 420b". As shown, one or more of the anchoring elements 410a", 410b", 410c" can overlap another anchor element to varying degrees. At least one advantage of such an overlap is a reduction in the overall length of the anchor 400". Such an overlap can also be used to achieve a desired force-versus-distance profile of the anchor 400", leading to a more gradual transition of the forces distributed along the axis.

Figure 6:
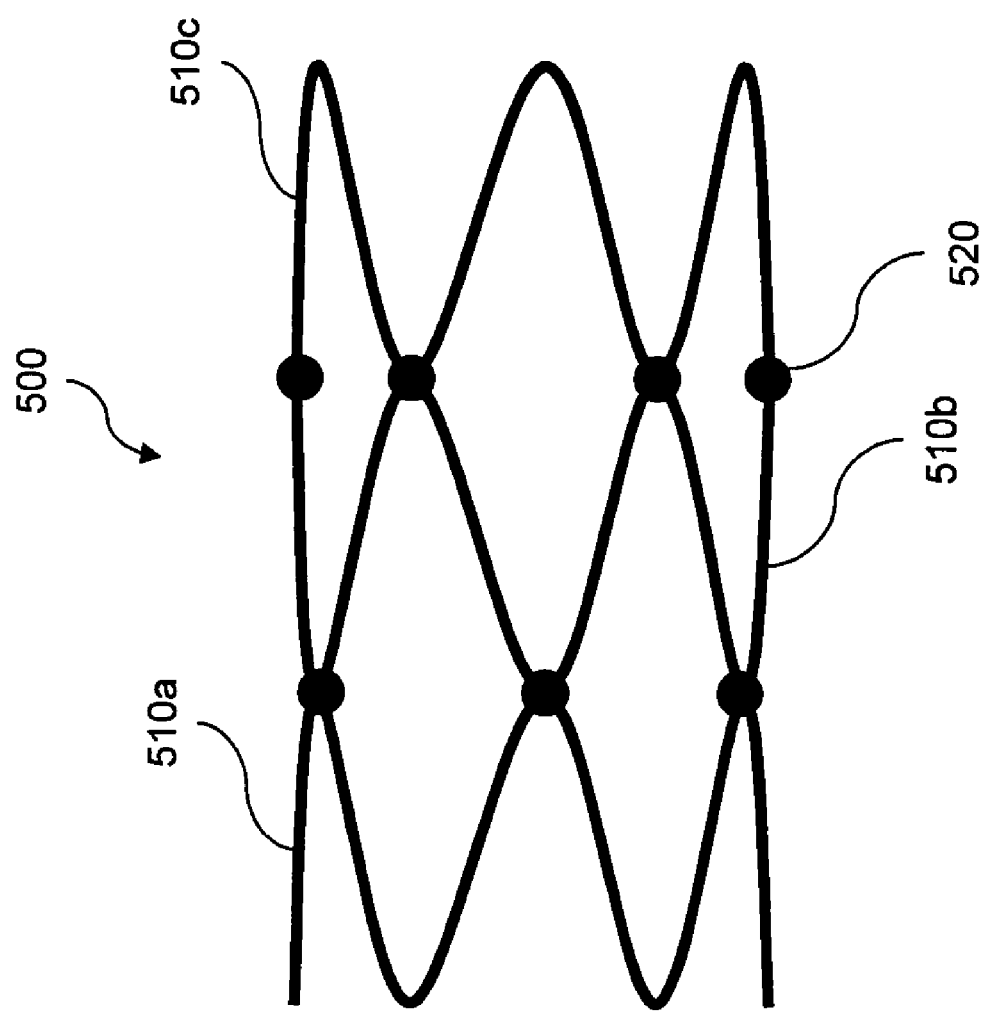
FIG. 6 is a schematic diagram illustrating an alternative embodiment of the intraluminal anchor shown in FIG. 4A having multiple coupled wave elements.

A side view of an alternative embodiment of an intraluminal anchor 500 is illustrated in FIG. 6. The anchor 500 includes multiple anchoring elements 510a, 510b, 510c, again shown as wave-shaped elements for illustrative purposes, that are interconnected to each other. The anchoring elements 510a, 510b, 510c can be interconnected by mechanical fasteners, chemical adhesives, thermal bonding, welding, soldering, and/or weaving. The interconnection may be fixed, or in the case of a weave, capable of longitudinal compression.

Figure 7:
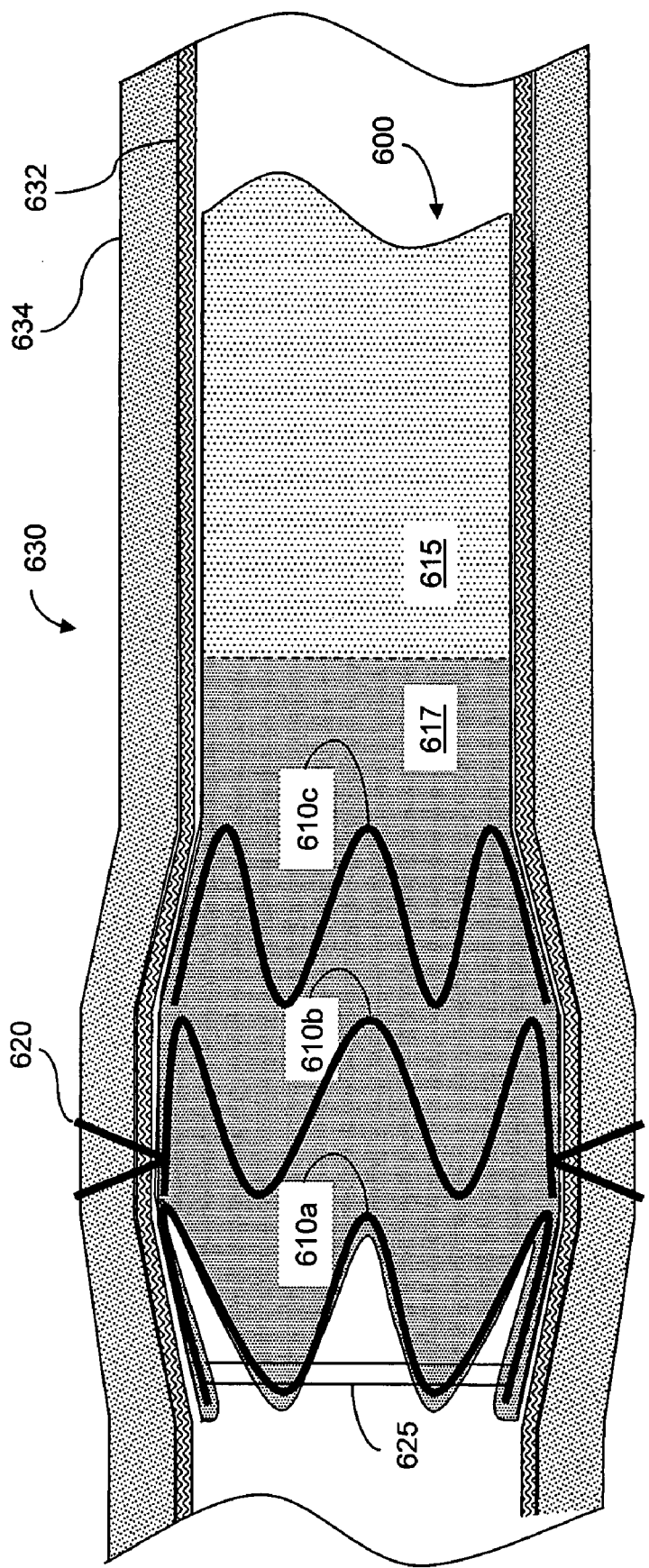
FIG. 7 is a schematic diagram illustrating a cross-sectional view of an embodiment of the intraluminal anchor device shown in FIG. 2 attached to a tube and implanted within a natural bodily lumen.

As described above, the intraluminal anchor can be used to anchor an elongated tube within a natural bodily lumen. An exemplary device 600 including an intraluminal anchor, similar to the one described above in reference to FIG. 5A, and coupled to the proximal end of an elongated tube 615 is illustrated in FIG. 7. The tube 615 may be rigid, semi-rigid or flexible. Gastrointestinal sleeves and related matters are described in U.S. application Ser. No. 10/339,786, filed Jan. 9, 2003, which claims the benefit of U.S. Provisional Application No. 60/430,321, filed Dec. 2, 2002; and U.S. application Ser. No. 10/726,011, filed on Dec. 2, 2003, which claims the benefit of U.S. Provisional Application No. 60/512,145 filed Oct. 17, 2003. The entire teachings of all of these applications are incorporated herein by reference.

The anchoring elements 610*a*, 610*b*, 610*c* (generally 610) can be bonded to the tube (e.g., chemically bonded using an adhesive, or thermally bonded). The anchoring elements 610 can also be mechanically coupled to the elongated tube 615. For example, the anchoring elements 610 can be coupled using a suture, a surgical staple, and/or by threading the anchoring element itself through perforations in the elongated tube.

In some embodiments, the anchoring elements 610 are encapsulated within the elongated tube 615. For example, the elongated tube 615 can be formed as a sleeve. A portion the sleeve can then be used to encapsulate the anchoring elements by folding one end of the sleeve back upon itself to cover both the interior and exterior of the anchoring elements 610. The portions of the elongated tube forming the overlapping portion 617 can then be coupled together, thereby capturing the anchoring elements 610 and securing them in place with respect to each other and with respect to the elongated tube 615. For example, the overlapping portions of the tube 617 can be bonded together (e.g., chemically bonded using an adhesive, or thermally bonded). Alternatively or in addition, the overlapping portions of the tube 617 can be mechanically fastened together. For example, the overlapping portions of the elongated tube 617 can be coupled together using sutures, staples, clasps, or any other suitable mechanical fastener.

As shown, the anchor 600 can include barbs 620 that protrude externally from the anchor 600 to penetrate the surrounding tissue. For illustrative purposes, the device 600 as implanted within a portion of an animal's intestine 630 illustrated in cross section. Shown are the intestinal wall 630 including an inner mucosal layer 632 in communication with the anchor 600 and a surrounding layer of muscular tissue 634. Preferably, the barbs 620 are adapted to penetrate the mucosal layer 632 and into the muscular tissue 634 of the intestine 630. In some embodiments, the barbs 620 actually penetrate the outer walls of the intestine 630. Thus, the barbs 620 provide an axial securing force component, with the anchoring element 610*b* providing a securing force adapted to maintain the barbs into engagement with the muscular tissue 634.

To ensure that the barbs 620 remain secured to the muscular tissue during implantation, the anchoring element to which the barbs 620 are coupled should be relatively stiff. Thus, the stiffness of the supporting anchoring element 610*b* maintains a radial force ensuring that the barbs 620 are driven into the tissue. In some embodiments, the stiffness is sufficient to force the supporting anchoring element 610*b* through the mucosal layer 632, abutting it to the layer of muscular tissue 634.

In some applications, however, the stiffness of the anchoring element 310*b* can lead to irritation and possibly damage to the surrounding tissue. To reduce the possibility of such irritation or damage, additional anchoring elements 610*a*, 610*c* are provided on either side of the anchoring element 610*b*. Preferably, the additional anchoring elements 610*a*, 610*c* are less stiff (i.e., softer) than the central anchoring element 610*b*. In this manner, the transition between unanchored portions of the lumen and the stiff anchoring element 610*b* is spread over a larger surface area to achieve the desired anchoring force at the barbs 620 in a gradual manner. Thus, the additional anchoring elements 610*a*, 610*c* provide a strain relief on both sides of the stiff anchoring element 610*b* to minimize trauma to the tissue, as shown in FIG. 1B.

Figure 8:
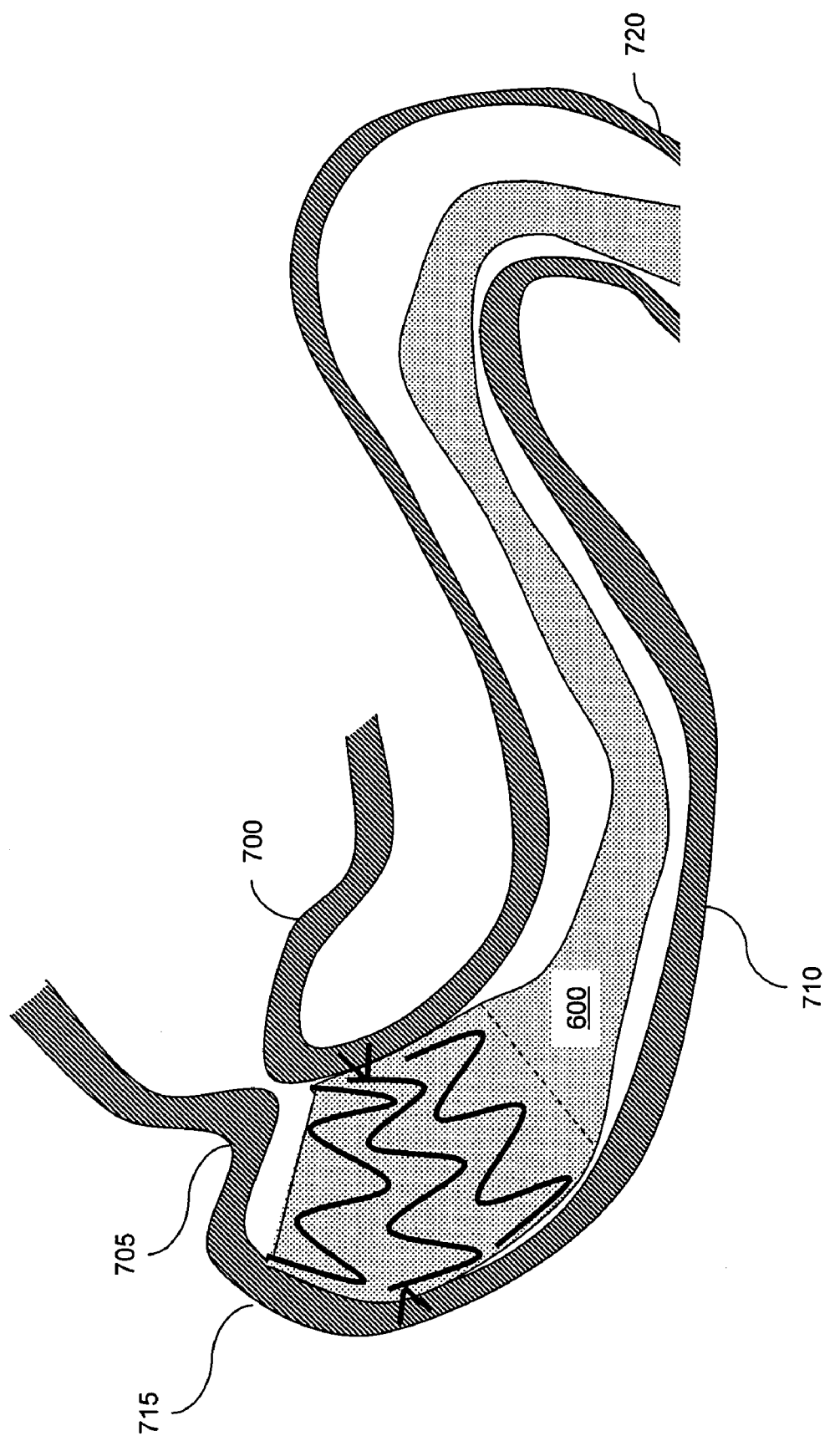
FIG. 8 is a schematic diagram illustrating a cross-sectional view of the intraluminal anchor device shown in FIG. 7 implanted within the proximal duodenum.

An exemplary embodiment of an intraluminal anchor anchoring an elongated flexible sleeve within the intestine of an animal is illustrated in FIG. 8. A lower portion of the stomach 700 is shown terminating in a pyloric sphincter 705. Distal to the sphincter 705 is the proximal duodenum 715, sometimes referred to as the duodenal bulb. The device of FIG. 7 is implanted with the anchor being situated distal to the pyloric sphincter 705, preferably within the duodenal bulb 715. The sleeve 600 can extend through the duodenum 710 and into the jejunum 720.

Figure 9A:
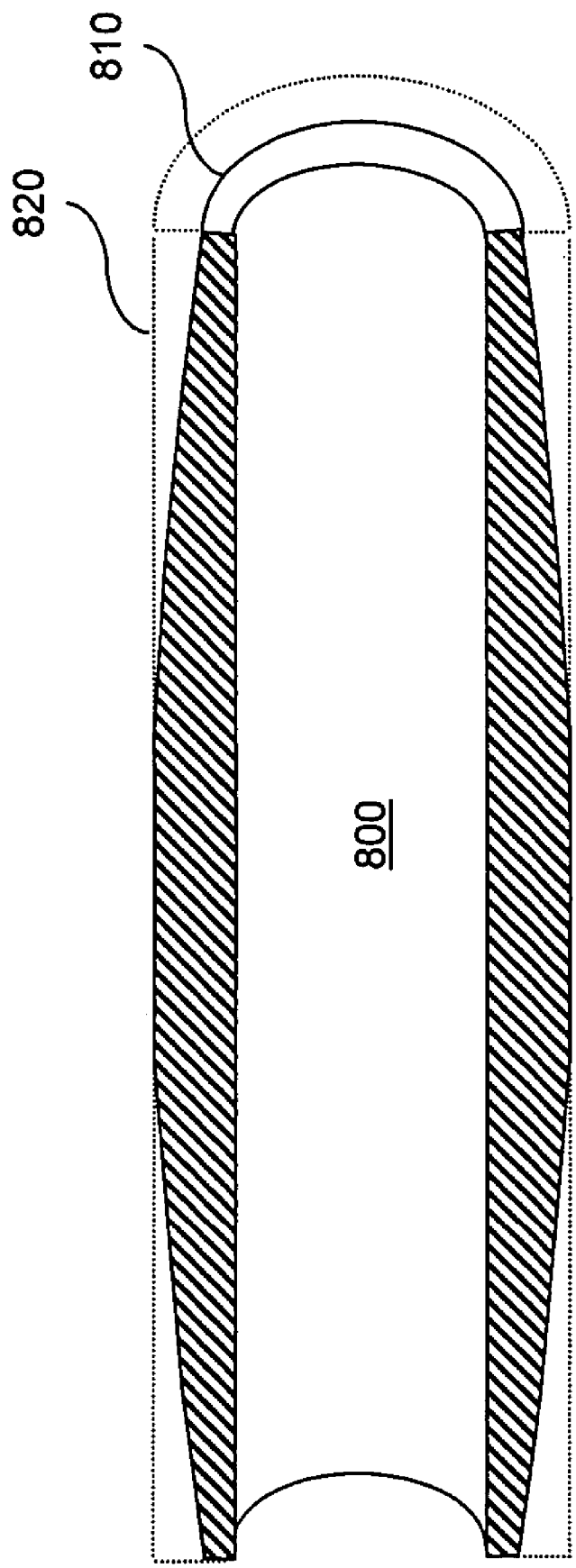
FIG. 9A is a schematic diagram illustrating an embodiment of a shaped tube.

As described above in reference to wire anchoring elements, the radial force, or stiffness can be controlled by varying a physical property of the anchoring element. This approach can also be extended beyond wire examples. For example, the elongated anchoring element can be formed from a tapered tube. To vary the radial force, or stiffness, the tube can be shaped to vary its wall thickness. The axial taper can be accomplished by injection moulding to a desired shape and/or by removing material from a solid elongated tube. The result in either case is an anchoring element having differing thicknesses along its central axis. FIG. 9A illustrates a cross-sectional view of an exemplary tube 800 after having both ends tapered from a thicker middle section. Thus, the thinner ends 810 are achieved by removing extra material 820. For example, a stainless steel or alloy (e.g., Nitinol) tube 800 can be shaped by grinding it and/or turning it on a lathe to selectably remove material along its length. As shown, the tube 800 can be tapered from a relatively thick portion along the tube middle, to a relatively thin portion at the tube's ends (with this approach, any conceivable profile is possible).

Figure 9B:
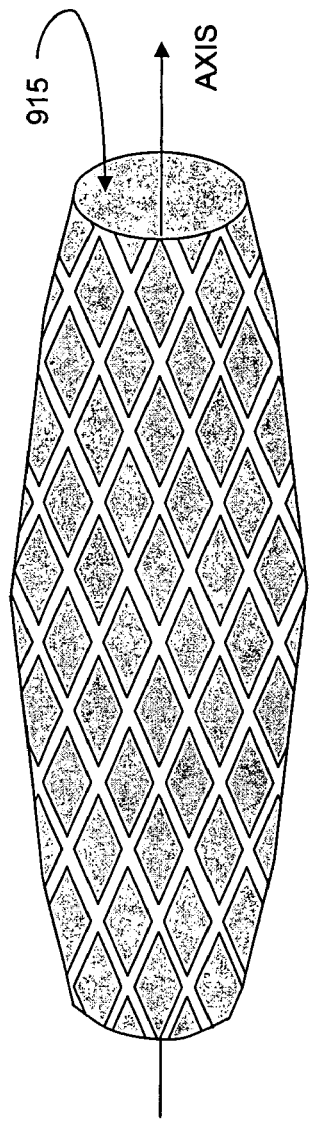
FIG. 9B is a schematic diagram illustrating an embodiment of an intraluminal anchor formed from the shaped tube shown in FIG. 9A.
Figure 9C:
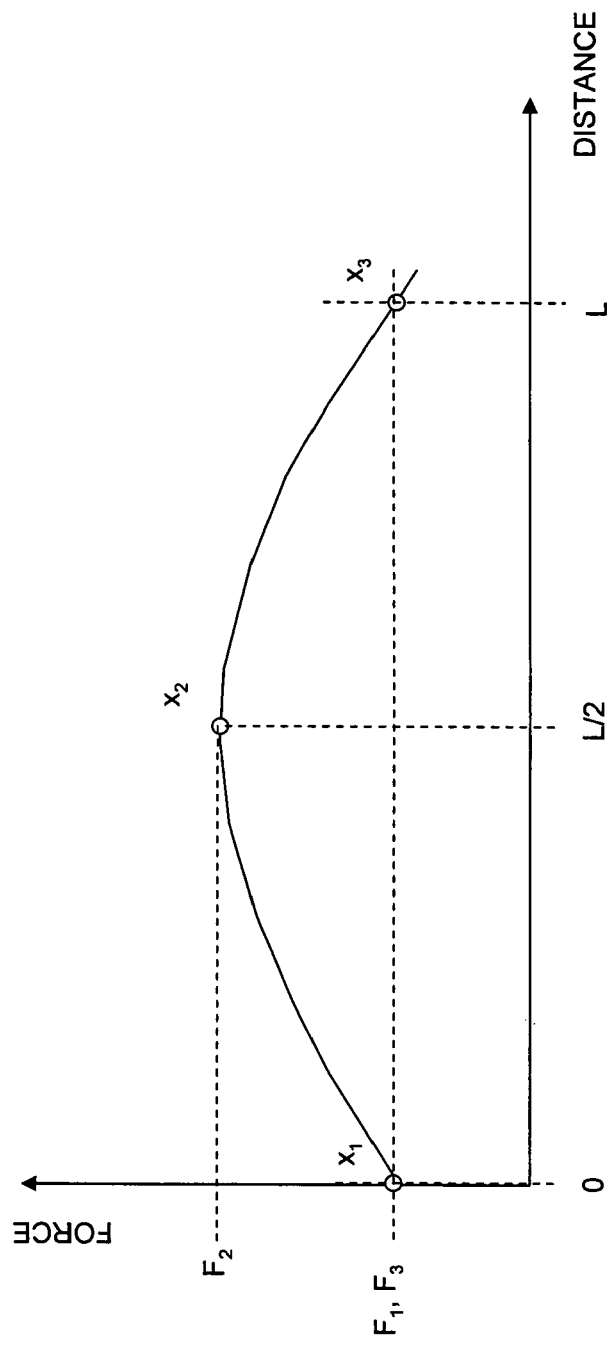
FIG. 9C is an exemplary radial-force profile for the intraluminal anchor of FIG. 9B.

The shaped tube 800, once tapered, can be further processed to form an expandable anchor. For example, referring to FIG. 9B, apertures 920 can be cut into the shaped tube 900 walls using a laser. The remaining portions of the shaped tube 910, once cut, can form a continuous structure such as the interconnected network of struts 910 shown, or even a wave structure as described above. Again, the resulting structure provides an interior lumen 915, while also being radially compressible. A corresponding force-versus-distance profile for the exemplary tube 900 is illustrated in FIG. 9C.

As will be appreciated by those of skill in the art, there are many potential variations to these methods and articles. Those variations are encompassed by this invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. An intraluminal implant comprising:
   an elongated anchor adapted for implanting within a natural bodily lumen, a central axis of the elongated anchor adapted for alignment with the natural bodily lumen, the elongated anchor including:
   a primary anchoring region adapted to expand against the lumen;
   a secondary anchoring region disposed at either side of the primary anchoring region also adapted to expand against the lumen, the primary anchoring region expanding to a greater extent than an outer end of each of the secondary anchoring regions;
   a flexible, floppy elongated sleeve coupled at its proximal end to the elongated anchor, the sleeve adapted to extend distally beyond the elongated anchor within the natural bodily lumen;
   the elongated anchor comprising;
   a plurality of anchoring elements, at least one of the anchoring elements relating to the primary anchoring region and at least two other of the anchoring elements relating to the secondary anchoring regions, a secondary anchoring element being on each side of the primary anchoring element.

2. The intraluminal anchor of claim 1, wherein the anchoring element relating to the primary anchoring region and the at least two other of the anchoring elements relating to the secondary anchoring regions comprise different materials.

3. The intraluminal anchor of claim 1, wherein the anchoring element relating to the primary anchoring region and the at least two other of the anchoring elements relating to the secondary anchoring regions comprise substantially the same material having a different thickness.

4. The intraluminal anchor of claim 1, wherein at least one of the plurality of anchoring elements is formed from an elongated wire.

5. The intraluminal anchor of claim 1, wherein at least one of the plurality of anchoring elements is a wave-shaped element.

6. The intraluminal anchor of claim 1, wherein at least one of the plurality of anchoring elements comprises at least one external barb in the primary anchoring region adapted to penetrate muscular tissue of the natural bodily lumen, the respective anchoring element expanding against the lumen and adapted to hold the barb within the muscular tissue.

7. The intraluminal anchor of claim 6, wherein the external barb is a bi-directional barb, comprising a first barb segment adapted to oppose proximal movement and a second barb segment adapted to oppose distal movement.

8. The intraluminal anchor of claim 1, further comprising at least one joining member coupled between at least two of the plurality of anchoring elements.

9. The intraluminal anchor of claim 1, wherein the elongated sleeve is adapted to be anchored in the proximal duodenum, the sleeve extending distally within the intestine.

10. The intraluminal anchor of claim 1, wherein the elongated sleeve is thin-walled, collapsing upon itself.

11. The intraluminal anchor of claim 1, further comprising at least one external barb positioned at the primary anchoring region and adapted to penetrate muscle of the natural bodily lumen, the expanding against the lumen adapted to hold the barb within the tissue.

12. The intraluminal anchor of claim 11, wherein the external barb is a bi-directional barb, comprising a first barb segment adapted to oppose proximal movement and a second barb segment adapted to oppose distal movement.

13. The intraluminal anchor of claim 1, wherein the elongated sleeve is adapted to be anchored in the proximal duodenum, the sleeve extending distally within the intestine.

14. The intraluminal anchor of claim 1, wherein the elongated sleeve is thin-walled, collapsing upon itself.

15. The intraluminal anchor of claim 1, wherein the elongated anchoring element is coupled to the sleeve between overlapping layers of the sleeve.

16. The intraluminal anchor of claim 1, wherein the anchor is radially collapsible for endoscopic insertion.

17. The intraluminal anchor of claim 1, wherein the elongated anchor is formed from a homogeneous hollow tube having a tube wall of differing thickness along its length, the tube wall defining apertures adapted to allow radial variation of the tube.

18. The intraluminal anchor of claim 1, wherein the primary and secondary anchoring regions comprise different spring rates.

19. The intraluminal anchor of claim 1, wherein the primary anchoring region is central.

20. The intraluminal anchor of claim 1, wherein at least one of the plurality of anchoring elements comprises at least one protrusion in the primary anchoring region adapted to be held within muscular tissue of the natural bodily lumen, the respective anchoring element expanding against the lumen and adapted to hold the protrusion within the muscular tissue.

21. The intraluminal anchor of claim 1, further comprising at least one protrusion positioned at the primary anchoring region and adapted to be held within muscular tissue of the natural bodily lumen, the expanding against the lumen adapted to hold the protrusion within the muscular tissue.

22. A method for anchoring a flexible, floppy elongated sleeve within a natural bodily lumen comprising:
providing an anchor fixed to a proximal end of the flexible, floppy elongated sleeve, the sleeve extending distally into the natural bodily lumen;
providing a radially-outward securing force from the anchor acting upon a first region of the natural bodily lumen;
providing a radially-outward transitional force from the anchor less than the securing force on the first region and acting upon a second region of the natural bodily lumen beside the first region of the natural bodily lumen, the radially-outward transitional force from the anchor acting on each side of the first region and being adapted to mitigate damage to the natural bodily lumen; and
piercing muscular tissue of the natural bodily lumen with at least one external barb in the first region, the radially outward securing force driving the at least one barb into the muscular tissue.

23. The method of claim 22, wherein a first anchoring elements providing the radially-outward securing force and a second anchoring element provides the radially-outward transitional force.

24. The method of claim 23, wherein the first and second anchoring elements comprise different spring rates.

25. The method of claim 22, further comprising inhibiting movement in either direction along the natural bodily lumen using the at least one barb.

26. The method of claim 22, further comprising at least partially radially collapsing the elongated anchoring element for insertion of the intraluminal anchor into the natural bodily lumen.

27. The method of claim 22, further comprising at least partially radially collapsing at least a portion of the elongated anchoring element for removal of the intraluminal anchor from the natural bodily lumen.

28. An intraluminal implant comprising:
an elongated anchor adapted for implanting within a natural bodily lumen, a central axis of the elongated anchor adapted for alignment with the natural bodily lumen, the elongated anchor including:
a primary anchoring region adapted to expand against the lumen;
a secondary anchoring region disposed at either side of the primary anchoring region also adapted to expand against the lumen, the primary anchoring region expanding to a greater extent than an outer end of each of the secondary anchoring regions, the primary and secondary anchoring regions comprising different spring rates; and
a flexible, floppy elongated sleeve coupled at its proximal end to the elongated anchor, the sleeve adapted to extend distally beyond the elongated anchor within the natural bodily lumen.

29. A method for anchoring a flexible, floppy elongated sleeve within a natural bodily lumen comprising:
providing an anchor fixed to a proximal end of the flexible, floppy elongated sleeve, the sleeve extending distally into the natural bodily lumen;

providing a radially-outward securing force from the anchor acting upon a first region of the natural bodily lumen, the radially outward securing force being provided by a first anchoring element; and providing a radially-outward transitional force from the anchor less than the securing force on the first region and acting upon a second region of the natural bodily lumen beside the first region of the natural bodily lumen, the radially outward transitional force being provided by a second anchoring element, the first and second anchoring elements comprising different spring rates, the radially-outward transitional force from the anchor acting on each side of the first region and being adapted to mitigate damage to the natural bodily lumen.

* * * * *